(12) United States Patent
Roy et al.

(10) Patent No.: US 8,148,321 B2
(45) Date of Patent: Apr. 3, 2012

(54) BIOCONJUGATES AS THERAPEUTIC AGENT AND SYNTHESIS THEREOF

(75) Inventors: Rajendra Prasad Roy, New Delhi (IN); Sharmishtha Samantaray, New Delhi (IN)

(73) Assignee: National Institute of Immunology, New Dehli, IN (US)

( * ) Notice: Subject to any disclaimer, the term of this patent is extended or adjusted under 35 U.S.C. 154(b) by 321 days.

(21) Appl. No.: 12/234,233

(22) Filed: Sep. 19, 2008

(65) Prior Publication Data

US 2009/0088372 A1    Apr. 2, 2009

Related U.S. Application Data

(63) Continuation of application No. PCT/IN2007/000115, filed on Mar. 21, 2007.

(30) Foreign Application Priority Data

Mar. 22, 2006    (IN) .............................. 797/DEL/2006

(51) Int. Cl.
*A61K 38/00* (2006.01)
*A61K 31/70* (2006.01)
*A01N 43/04* (2006.01)
(52) U.S. Cl. .............................. 514/1.1; 514/23; 514/42
(58) Field of Classification Search .......................... None
See application file for complete search history.

(56) References Cited

U.S. PATENT DOCUMENTS 3,928,583 A * 12/1975 Furuno et al. .................... 514/37
2003/0153020 A1   8/2003 Schneewind et al.

FOREIGN PATENT DOCUMENTS

| CA | 2094658 A1 | 10/1993 |
|---|---|---|
| WO | WO 99/67284 A2 | 12/1999 |
| WO | WO 2005/051976 A2 | 6/2005 |
| WO | WO 2006/115312 A1 | 11/2006 |
| WO | WO 2006/125165 A2 | 11/2006 |

OTHER PUBLICATIONS

Alexander Litovchick et al.; Neomycin B-Arginine Conjugate, a Novel HIV-1 Tat Antagonist: Synthesis and Anti-HIV Activities; publication; 2001; 12 pages, pp. 15612-15623; Biochemistry; vol. 40, No. 51; American Chemical Society.
Alexander Litovchick et al.; Aminoglycoside-Arginine Conjugates That Bind TAR RNA: Synthesis, Characterization, and Antiviral Activity; publication; 2000;15 pages, pp. 2838-2852; Biochemistry; vol. 39, No. 11; American Chemical Society.
Timothy D. Eubank et al.; Inhibition of bacterial RNase P by aminoglycoside-arginine conjugates; publication; 2002, 6 pages, pp. 107-112; FEBS Letters 511; Elsevier Science B.V.
Luciano A. Marraffini et al.; Sortases and the Art of Anchoring Proteins to the Envelopes of Gram-Positive Bacteria; publication; 2006; 30 pages, pp. 192-221; Microbiology and Molecular Biology Reviews; vol. 70, No. 1; American Society for Microbiology.
Ranganath Parthasarathy et al.; Sortase A as a Novel Molecular "Stapler" for Sequence-Specific Protein Conjugation; publication; 2007; 8 pages, pp. 469-476; Bioconjugate Chem.; vol. 18, No. 2; American Chemical Society.
Stephan Pritz et al.; Synthesis of Biologically Active Peptide Nucleic Acid-Peptide Conjugates by Sortase-Mediated Ligation; publication; 2007; 4 pages, pp. 3909-3912; J. Org. Chem.; vol. 72, No. 10; American Chemical Society.
Ashraf Brik et al.; Sugar-Assisted Ligation of N-Linked Glycopeptides with Broad Sequence Tolerance at the Ligation Junction; publication; 2006; 8 pages, pp. 15026-15033; J. Am. Chem. Soc.; vol. 128, No. 46; American Chemical Society.
Ashraf Brik et al.; Strategies for the preparation of homogenous glycoproteins; publication; 2006; 7 pages, pp. 638-644; Current Opinion in Chemical Biology; vol. 10; Elsevier.
Bin Wu et al.; Building Complex Glycopeptides: Development of a Cysteine-Free Native Chemical Ligation Protocol; publication; 2006; 10 pages, pp. 4116-4125; Angew. Chem. Int. Ed.; vol. 45; Wiley-VCH Verlag GmbH & Co. KGaA, Weinheim.
Therese Buskas et al.; Glycopeptides as versatile tools for glycobiology; publication; 2006; 24 pages, pp. 113R-136R; Glycobiology; vol. 16, No. 8; Oxford University Press.
Katie J. Doores et al.; Exploring and Exploiting the Therapeutic Potential of Glycoconjugates; publication; 2006; 10 pages, pp. 656-665; Chem. Eur. J.; vol. 12; Wiley-VCH Verlag GmbH & Co. KGaA, Weinheim.
Pamela Sears et al.; Toward Automated Synthesis of Oligosaccharides and Glycoproteins; magazine; 2001; 7 pages, pp. 2344-2350; Science; vol. 291; American Association for the Advancement of Science, Washington, DC.
Hung Ton-That et al.; Purification and characterization of sortase, the transpeptidase that cleaves surface proteins of *Staphylococcus aureus* at the LPXTG motif; publication; 1999; 6 pages, pp. 12424-12429; PNAS; vol. 96, No. 22; Biochemistry.
Hongyuan Mao et al.; Sortase-Mediated Protein Ligation: A New Method for Protein Engineering; publication; 2004; 2 pages, pp. 2670-2671; J. Am. Chem. Soc.; vol. 126, No. 9; American Chemical Society.
Kathryn M. Koeller et al.; Synthesis of Complex Carbohydrates and Glycoconjugates: Enzyme-Based and Programmable One-Pot Strategies; publication; 2000; 29 pages, pp. 4465-4493; Chemical Reviews; vol. 100, No. 12; American Chemical Society.

* cited by examiner

*Primary Examiner* — Marcela M Cordero Garcia
(74) *Attorney, Agent, or Firm* — Reinhart Boerner Van Deuren P.C.

(57) ABSTRACT

The present disclosure relates to a novel enzymatic approach according to the invention using an unprecedented sortase-catalyzed transpeptidation reaction between a substrate comprising LPXTG (SEQ ID NO: 11) peptide motif and biomolecules such as aminosugars, hydroxyamino acids, hydroxyamino acid esters, aminolipids, polyamines; nucleic acids or derivatives thereof; or any molecule having such moieties; or any compound having such moieties to obtain a bioconjugates useful for target delivery of a compound. The present disclosure provides bioconjugates obtained by the novel sortase catalysed transpeptidedation reaction.

15 Claims, 10 Drawing Sheets

SEQUENCE LISTING

<160> NUMBER OF SEQ ID NOS: 27

<210> SEQ ID NO 1
<211> LENGTH: 8
<212> TYPE: PRT
<213> ORGANISM: ARTIFICIAL
<220> FEATURE:
<223> OTHER INFORMATION: SYNTHETIC SEQUENCE

<400> SEQUENCE: 1

Tyr Ala Leu Pro Glu Thr Gly Lys
1               5

<210> SEQ ID NO 2
<211> LENGTH: 8
<212> TYPE: PRT
<213> ORGANISM: ARTIFICIAL
<220> FEATURE:
<223> OTHER INFORMATION: SYNTHETIC SEQUENCE

<400> SEQUENCE: 2

Tyr Ala Leu Pro Met Thr Gly Lys
1               5

<210> SEQ ID NO 3
<211> LENGTH: 15
<212> TYPE: PRT
<213> ORGANISM: ARTIFICIAL
<220> FEATURE:
<223> OTHER INFORMATION: SYNTHETIC SEQUENCE

<400> SEQUENCE: 3

Arg Arg Arg Arg Arg Arg Arg Arg Arg Leu Pro Glu Thr Gly Lys
1               5                   10                  15

<210> SEQ ID NO 4
<211> LENGTH: 15
<212> TYPE: PRT
<213> ORGANISM: ARTIFICIAL
<220> FEATURE:
<223> OTHER INFORMATION: SYNTHETIC SEQUENCE

<400> SEQUENCE: 4

Arg Arg Arg Arg Arg Arg Arg Arg Arg Leu Pro Met Thr Gly Lys
1               5                   10                  15

<210> SEQ ID NO 5
<211> LENGTH: 26
<212> TYPE: PRT
<213> ORGANISM: ARTIFICIAL
<220> FEATURE:
<223> OTHER INFORMATION: SYNTHETIC SEQUENCE

<400> SEQUENCE: 5

Thr Arg Gln Ala Arg Arg Asn Arg Arg Arg Trp Arg Glu Arg Gln
1               5                   10                  15

Arg Gly Gly Gly Leu Pro Glu Thr Gly Lys
                20                  25

<210> SEQ ID NO 6
<211> LENGTH: 33
<212> TYPE: DNA
<213> ORGANISM: ARTIFICIAL
<220> FEATURE:
<223> OTHER INFORMATION: SYNTHETIC SEQUENCE

```
<400> SEQUENCE: 6
gatatacata tgcaagctaa acctcaaatt ccg                         33

<210> SEQ ID NO 7
<211> LENGTH: 36
<212> TYPE: PRT
<213> ORGANISM: ARTIFICIAL
<220> FEATURE:
<223> OTHER INFORMATION: SYNTHETIC PEPTIDE

<400> SEQUENCE: 7
```

Gly Thr Gly Gly Thr Gly Cys Thr Cys Gly Ala Gly Thr Thr Gly
1               5                   10                  15

Ala Cys Thr Thr Cys Thr Gly Thr Ala Gly Cys Thr Ala Cys Ala Ala
            20                  25                  30

Ala Gly Ala Thr
        35

```
<210> SEQ ID NO 8
<211> LENGTH: 6
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 8
```

Tyr Ala Leu Pro Glu Thr
1               5

```
<210> SEQ ID NO 9
<211> LENGTH: 6
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 9
```

Tyr Ala Leu Pro Met Thr
1               5

```
<210> SEQ ID NO 10
<211> LENGTH: 25
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 10
```

Thr Arg Gln Ala Arg Arg Asn Arg Arg Arg Arg Trp Arg Glu Arg
1               5                   10                  15

Gln Arg Gly Gly Gly Leu Pro Glu Thr
            20                  25

```
<210> SEQ ID NO 11
<211> LENGTH: 5
<212> TYPE: PRT
<213> ORGANISM: ARTIFICIAL
<220> FEATURE:
<223> OTHER INFORMATION: SYNTHETIC SEQUENCE
<220> FEATURE:
<221> NAME/KEY: MISC_FEATURE
<222> LOCATION: (3)..(3)
<223> OTHER INFORMATION: Any Amino Acid

<400> SEQUENCE: 11
```

Leu Pro Xaa Thr Gly

```
<210> SEQ ID NO 12
<211> LENGTH: 5
<212> TYPE: PRT
<213> ORGANISM: ARTIFICIAL
<220> FEATURE:
<223> OTHER INFORMATION: SYNTHETIC SEQUENCE

<400> SEQUENCE: 12

Gly Gly Gly Gly Gly
1               5

<210> SEQ ID NO 13
<211> LENGTH: 9
<212> TYPE: PRT
<213> ORGANISM: ARTIFICIAL
<220> FEATURE:
<223> OTHER INFORMATION: SYNTHETIC SEQUENCE
<220> FEATURE:
<221> NAME/KEY: MISC_FEATURE
<222> LOCATION: (3)..(3)
<223> OTHER INFORMATION: Any Amino Acid

<400> SEQUENCE: 13

Leu Pro Xaa Thr Gly Gly Gly Gly Gly
1               5

<210> SEQ ID NO 14
<211> LENGTH: 6
<212> TYPE: PRT
<213> ORGANISM: ARTIFICIAL
<220> FEATURE:
<223> OTHER INFORMATION: SYNTHETIC SEQUENCE

<400> SEQUENCE: 14

Thr Glu Pro Leu Ala Tyr
1               5

<210> SEQ ID NO 15
<211> LENGTH: 13
<212> TYPE: PRT
<213> ORGANISM: ARTIFICIAL
<220> FEATURE:
<223> OTHER INFORMATION: SYNTHETIC SEQUENCE

<400> SEQUENCE: 15

Arg Arg Arg Arg Arg Arg Arg Arg Arg Leu Pro Met Thr
1               5                   10

<210> SEQ ID NO 16
<211> LENGTH: 6
<212> TYPE: PRT
<213> ORGANISM: ARTIFICIAL
<220> FEATURE:
<223> OTHER INFORMATION: SYNTHETIC SEQUENCE

<400> SEQUENCE: 16

Tyr Ala Leu Pro Glu Thr
1               5

<210> SEQ ID NO 17
<211> LENGTH: 6
<212> TYPE: PRT
<213> ORGANISM: ARTIFICIAL
<220> FEATURE:
<223> OTHER INFORMATION: SYNTHETIC SEQUENCE
<220> FEATURE:
<221> NAME/KEY: MISC_FEATURE
```

```
<222> LOCATION: (3)..(3)
<223> OTHER INFORMATION: Any Amino Acid

<400> SEQUENCE: 17

Leu Pro Xaa Thr Gly Lys
1               5

<210> SEQ ID NO 18
<211> LENGTH: 15
<212> TYPE: PRT
<213> ORGANISM: ARTIFICIAL
<220> FEATURE:
<223> OTHER INFORMATION: SYNTHETIC PROTEIN
<220> FEATURE:
<221> NAME/KEY: MISC_FEATURE
<222> LOCATION: (12)..(12)
<223> OTHER INFORMATION: Any Amino Acid

<400> SEQUENCE: 18

Arg Arg Arg Arg Arg Arg Arg Arg Arg Leu Pro Xaa Thr Gly Lys
1               5                   10                  15

<210> SEQ ID NO 19
<211> LENGTH: 8
<212> TYPE: PRT
<213> ORGANISM: ARTIFICIAL
<220> FEATURE:
<223> OTHER INFORMATION: SYNTHETIC SEQUENCE
<220> FEATURE:
<221> NAME/KEY: MISC_FEATURE
<222> LOCATION: (5)..(5)
<223> OTHER INFORMATION: Any Amino Acid

<400> SEQUENCE: 19

Tyr Ala Leu Pro Xaa Thr Gly Lys
1               5

<210> SEQ ID NO 20
<211> LENGTH: 20
<212> TYPE: PRT
<213> ORGANISM: ARTIFICIAL
<220> FEATURE:
<223> OTHER INFORMATION: SYNTHETIC SEQUENCE

<400> SEQUENCE: 20

Thr Arg Gln Ala Arg Arg Asn Arg Arg Arg Trp Arg Glu Arg Gln
1               5                   10                  15

Arg Gly Gly Gly
            20

<210> SEQ ID NO 21
<211> LENGTH: 8
<212> TYPE: PRT
<213> ORGANISM: ARTIFICIAL
<220> FEATURE:
<223> OTHER INFORMATION: SYNTHETIC SEQUENCE

<400> SEQUENCE: 21

Tyr Ala Leu Met Pro Thr Gly Lys
1               5

<210> SEQ ID NO 22
<211> LENGTH: 15
<212> TYPE: PRT
<213> ORGANISM: ARTIFICIAL
<220> FEATURE:
<223> OTHER INFORMATION: SYNTHETIC SEQUENCE

<400> SEQUENCE: 22
```

```
Arg Arg Arg Arg Arg Arg Arg Arg Leu Pro Met Thr Gly Lys
1               5                   10                  15
```

<210> SEQ ID NO 23
<211> LENGTH: 15
<212> TYPE: PRT
<213> ORGANISM: ARTIFICIAL
<220> FEATURE:
<223> OTHER INFORMATION: SYNTHETIC SEQUENCE

<400> SEQUENCE: 23

```
Arg Arg Arg Arg Arg Arg Arg Arg Leu Pro Glu Thr Gly Lys
1               5                   10                  15
```

<210> SEQ ID NO 24
<211> LENGTH: 8
<212> TYPE: PRT
<213> ORGANISM: ARTIFICIAL
<220> FEATURE:
<223> OTHER INFORMATION: SYNTHETIC SEQUENCE

<400> SEQUENCE: 24

```
Tyr Ala Leu Pro Glu Thr Gly Lys
1               5
```

<210> SEQ ID NO 25
<211> LENGTH: 6
<212> TYPE: PRT
<213> ORGANISM: Artificial
<220> FEATURE:
<223> OTHER INFORMATION: Regulator of Virion

<400> SEQUENCE: 25

```
Leu Pro Glu Thr Gly Lys
1               5
```

<210> SEQ ID NO 26
<211> LENGTH: 13
<212> TYPE: PRT
<213> ORGANISM: ARTIFICIAL
<220> FEATURE:
<223> OTHER INFORMATION: SYNTHETIC SEQUENCE

<400> SEQUENCE: 26

```
Thr Glu Pro Leu Arg Arg Arg Arg Arg Arg Arg Arg
1               5                   10
```

<210> SEQ ID NO 27
<211> LENGTH: 6
<212> TYPE: PRT
<213> ORGANISM: ARTIFICIAL
<220> FEATURE:
<223> OTHER INFORMATION: SYNTHETIC SEQUENCE

<400> SEQUENCE: 27

```
Thr Met Pro Leu Ala Tyr
1               5
```

BIOCONJUGATES AS THERAPEUTIC AGENT AND SYNTHESIS THEREOF

CROSS-REFERENCE TO RELATED PATENT APPLICATIONS

This patent application is a continuation of co-pending PCT Application No. PCT/IN2007/000115, filed Mar. 21, 2007, which claims the benefit of Indian Patent Application No. 797/DEL/2006, filed Mar. 22, 2006, the entire teachings and disclosure of which are incorporated herein by reference thereto.

FIELD OF INVENTION

The present disclosure provides bioconjugates for target delivery of a compound wherein the bioconjugates are useful as therapeutic and/or diagnostic agent. The disclosure further provides a process for preparation of the bioconjugates.

BACKGROUND OF THE INVENTION

Development of new methods for linking sugars to peptides or proteins is an active area of research (Brik A, Ficht S, Yang Y Y, Bennett C S and Wong C-H (2006) J Am Chem Soc 128: 15026-33; Brik A, Ficht S and Wong C-H (2006) Curr Opin Struct Biol 10: 638-44; Wu B, Chen J, Warren J D, Chen G, Hua Z and Danishefsky S J (2006) Angew Chem 45: 4116-45; Buskas J, Ingale S and Boons G J (2006) Glycobiology 16: 113R-136R.), because natural or neoglycoconjugates play important roles in biology and medicine and are indispensable tools for probing several biological processes (Doores K J, Gamblin D P and Davis B G (2006) Chem Eur J 12: 656-665).

However, despite dramatic progress in synthetic carbohydrate and protein chemistry in recent years, glycoconjugate synthesis involving sugar and a polypeptide remains a formidable task. This is principally because synthetic protocols are quite demanding and involve multiple reaction steps with requirements of rather extensive protection of reactive functionalities. The problem may be in part or completely obviated through the intermediary of enzymes. Indeed, glycosidases and glycosyl transferases, in appropriate situations, have made the oligosaccharide synthesis much simpler (Koeller K M and Wong C-H (2000) Chem Rev 100: 4465; Sears P and Wong C-H (2001) Science 291: 2344-2350.)

Given the current ease with which peptides are assembled by solid phase methodology and proteins obtained from expression systems, the availability of an enzyme capable of covalently linking a pre-synthesized sugar and a polypeptide would greatly facilitate the 'convergent' semisynthesis of glycopeptide or protein mimetics (neoglycoconjugates) with exquisite biological properties.

The bacterial transpeptidase sortase, present in the cell envelop of most gram-positive organisms, catalyzes the covalent anchoring of several virulence-related bacterial surface proteins to the peptidoglycan cross-bridges of the cell wall (Marraffini L A, Dedent A C and Schneewind O (2006) Microbiol Mol Biol Rev 70: 192-221). Sortase A of *Staphylococcus aureus* recognizes a LPXTG (SEQ ID NO: 11) like sequence motif located near the C-terminus of the target proteins, cleaves at Thr-Gly peptide bond, and catalyzes the formation of a new peptide bond between threonyl carboxyl and amino group of the peptidoglycan penta-glycine cross-bridges (Marraffini L A, Dedent A C and Schneewind O (2006) Microbiol Mol Biol Rev 70: 192-221; Ton-That H, Liu G, Mazmanian S K, Faull K F and Schneewind O (1999) Proc Natl Acad Sci USA 96: 12424-29). This is illustrated below:
—LPXTG (SEQ ID NO: 11)—+GGGGG (SEQ ID NO: 12)—→—LPXTGGGGG (SEQ ID NO: 13)—+G—

The transpeptidation reaction proceeds in two steps without the aid of ATP or any other extraneous molecule; active site cysteine residue first attacks the target LPXTG (SEQ ID NO: 11) substrate forming and acyl-enzyme intermediate which in the second step is resolved by the nucleophilic attack of the amino group of terminal Gly residue of the peptidoglycan. In the absence of a suitable amino nucleophile, LPXTG (SEQ ID NO: 11) peptide substrate is slowly hydrolyzed (Marraffini L A, Dedent A C and Schneewind O (2006) Microbiol Mol Biol Rev 70: 192-221; Ton-That H, Liu G, Mazmanian S K, Faull K F and Schneewind O (1999) Proc Natl Acad Sci USA 96: 12424-29). The ligation of LPXTG containing short or long polypeptide sequences to polypeptide fragments containing even a single Gly residue at the amino terminal has been shown to proceed in vitro (Mao H, Hart S A, Schink A and Pollok B A (2004) J Am Chem Soc 126: 2670-71). Mao et al (2004) have recently demonstrated the utility of sortase-mediated protein ligation as a tool for protein engineering by applying this approach to the synthesis of protein-peptide conjugates that would have been rather difficult to obtain by chemical or genetic methods.

SUMMARY OF THE INVENTION

The present disclosure provides bioconjugates for target delivery of a compound wherein the bioconjugates are useful as therapeutic and/or diagnostic agent. The disclosure further provides a process for preparation of the bioconjugates.

In one aspect, the present disclosure provides therapeutic and/or diagnostic bioconjugates useful for target delivery of a compound, wherein the bioconjugate comprises:
  a. a substrate comprising LPXTG (SEQ ID NO: 11) peptide motif capable of recognizing sortase, wherein said substrate is selected from a group consisting of peptides, polypeptides, proteins, glycoprotein, lipoprotein, antibodies, radionucleotides, fluorophores, ligand chromophore and any compound comprising the LPXTG (SEQ ID NO: 11) peptide motif; and
  b. a biomolecule selected from a group consisting of aminoglycoside, polyamines, aminosugars, hydroxyamino acids, hydroxyamino acid esters, aminolipids and any other compound comprising these moieties.

In another aspect, the present disclosure provides a process for preparation of the bioconjugate, wherein the process comprises:
  a. providing a substrate comprising LPXTG (SEQ ID NO: 11) peptide motif capable of recognizing sortase, wherein said substrate is selected from a group consisting of peptides, polypeptides, proteins, glycoprotein, lipoprotein, antibodies, radionucleotides, fluorophores, ligand chromophore and any compound comprising the LPXTG (SEQ ID NO: 11) peptide motif;
  b. providing a biomolecule selected from a group consisting of aminoglycoside, aminosugars, polyamines, hydroxyamino acids, hydroxyamino acid esters aminolipids and any compound comprising these moieties;
  c. providing sortase to catalyze the ligation reaction of said substrate and said biomolecule under suitable conditions to obtain said bioconjugate.

In yet another aspect, the present disclosure provides a composition useful as therapeutic or diagnostic agent comprising the bioconjugate disclosed in the present invention and pharmaceutically acceptable salts thereof.

In still another aspect, the present disclosure provides a kit useful for therapy and/or diagnosis wherein the kit comprises the bioconjugate of the present invention and reagents suitable for administering said bioconjugate to an individual.

BRIEF DESCRIPTION OF ACCOMPANYING DRAWINGS

DETAILED DESCRIPTION OF THE INVENTION

Definitions

Figure 1:
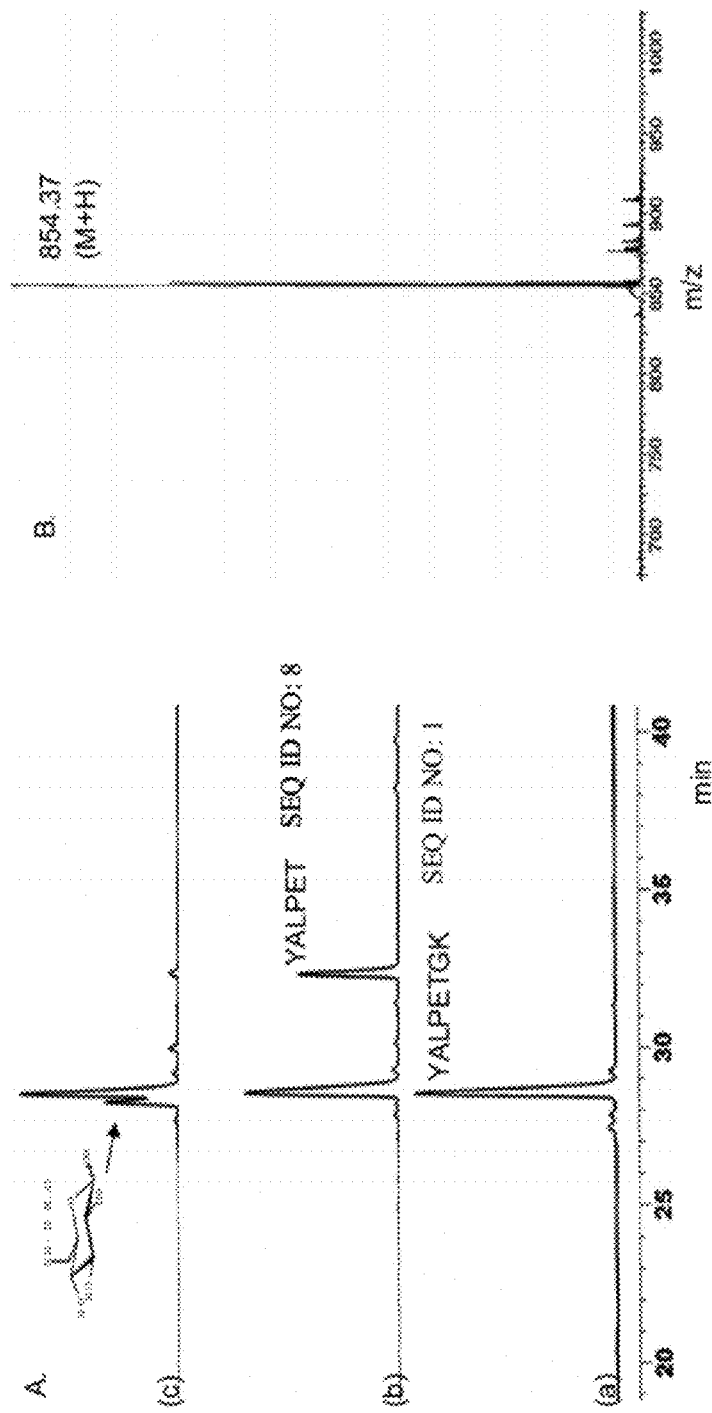
FIG. 1 shows analyses (RPHLC and mass) of the Sortase-catalyzed conjugation reaction of YALPETGK (SEQ ID NO: 1) to aminosugars.

The term "Biomolecule" used herein means a biologically relevant molecule that is used to contact molecular entities in a test sample. These biomolecule include at least in part, molecules such as aminosugars, hydroxyamino acids, hydroxyamino acid esters, aminolipids, polyamines, proteins, peptides, enzymes, and antibodies or derivatives thereof; or any molecule having such moieties; or any compound having such moieties. Biomolecules also include unnatural or synthetic molecules structurally derived from the naturally occurring molecules such as aminosugars, hydroxyamino acids, hydroxyamino acid esters, aminolipids, polyamines, proteins, peptides, enzymes, and antibodies or derivatives thereof; or any molecule having such moieties; or any compound having such moieties.

The term "polypeptide" is also intended to denote a peptide or a protein, these three terms being used interchangeably in the present disclosure.

The present disclosure provides bioconjugates useful for therapy and/or diagnosis. The present disclosure further provides a method for the preparation of the bioconjugates by a novel sortase catalyzed mechanism.

Bioconjugation is a descriptive term for the joining of two or more different molecular species by chemical or biological means, in which at least one of the molecular species is a biological macromolecule. This includes, but is not limited to conjugation of proteins, peptides, polypeptides, polysaccharides, hormones, nucleic acids, and liposomes with each other or with any other molecular species that add useful properties, including, but not limited to, drugs, radionuclides, toxins, haptens, inhibitors, chromophores, fluorophores, ligands etc. Immobilization of biological macromolecules is also considered a special case of bioconjugation in which the macromolecule is conjugated, either reversibly or irreversibly, to an insoluble solid phase support. Bioconjugation is utilized extensively in biochemical, immunochemical and molecular biological research. Major applications of bioconjugation include; detection of gene probes, enzyme-linked immuno solid-phase assay, and monoclonal antibody drug targeting and medical imaging.

Bioconjugates are generally classified as either direct or indirect conjugates. Direct conjugates encompass those in which two or more components are joined by direct covalent chemical linkages. Alternatively, indirect conjugates encompass those in which two or more components are joined via an intermediary complex involving a biological molecule.

Surprisingly, the inventors have shown a novel enzymatic approach according to the invention using an unprecedented sortase-catalyzed transpeptidation reaction between substare comprising the LPXTG (SEQ ID NO: 11) peptide motif and biomolecules such as aminosugars, hydroxyamino acids, hydroxyamino acid esters, aminolipids, polyamines; nucleic acids or derivatives thereof; or any molecule having such moieties; or any compound having such moieties to obtain a bioconjugates useful for target delivery of a compound.

The present disclosure relates to a novel sortase-catalyzed transpeptidation reaction that leads to amide bond formation between the Threonyl carboxyl of an LPXTG (SEQ ID NO: 11) motif of a substrate and aminosugar such as (hexoaminosugar) hexoses for example 6-amino-6-deoxyhexose for example 6-amino-6-deoxyglucose, 6-amino-6-deoxymannose, 6-amino-6-deoxyallose, 6-amino-6-deoxyaltrose, 6-amino-6-deoxyidose, 6-amino-6-deoxygalactose and 6-amino-6-deoxytalose.

The present disclosure further relates to a novel sortase-catalyzed transpeptidation reaction that leads to amide bond formation between the Threonyl carboxyl of an LPXTG (SEQ ID NO: 11) motif of a substrate and hydroxyamino acids (or derivatives thereof) such as 4-amino-3-hydroxybutyric acid and 4-amino-2-hydroxybutyric acid.

The present disclosure further relates to a novel sortase-catalyzed transpeptidation reaction that leads to amide bond formation between the Threonyl carboxyl of an LPXTG (SEQ ID NO: 11) motif of a substrate and hydroxyamino acid esterified with alkyl, aromatic and other specific molecular entities such as a cofactor (coenzyme A), Viz., 4-amino-3-hydroxybutyryl-coenzyme A, 4-amino-2-hydroxy-butyryl-coenzyme A.

The present disclosure further relates to a novel sortase-catalyzed transpeptidation reaction that leads to amide bond formation between the Threonyl carboxyl of an LPXTG (SEQ ID NO: 11) motif of a substrate and aminolipids such as lipoamino acid containing lipids viz., N-[(3-hexadecanoyloxy)hexadecanoyl]ornithine and ethanolamine lipids such as virodhamine.

The present disclosure further relates to a novel sortase-catalyzed transpeptidation reaction that leads to amide bond formation between the Threonyl carboxyl of an LPXTG (SEQ ID NO: 11) motif of a substrate and polyamines such as spermine, spermidine and agmatine.

The present disclosure provides a method of preparation of bioconjugates using a sortase catalyzed transpeptidation reaction between peptides comprising the LPXTG (SEQ ID NO: 11) peptide motif and biomolecules such as aminosugars, hydroxyamino acids, hydroxyamino acid esters, aminolipids, polyamines; or derivatives thereof; or any molecule having such moieties; or any compound having such moieties to obtain a bioconjugates useful for target delivery of a compound. The utility of this reaction is further demonstrated in the preparation of bioconjugates consisting of peptides and aminoglycoside antibiotics. Also, since sortases are known as important therapeutic targets for combating infectivity of gram-positive bacteria the above substrate-mimetic amino sugar scaffold is useful for designing an aminosugar based inhibitor of the enzyme.

The potential of sortase to ligate LPXTG (SEQ ID NO: 11) containing substrates to different aminosugar moieties to form glycopeptides was tested by the inventors. A bioconjugates was obtained by sortase catalyzed ligation of LPXTG (SEQ ID NO: 11) containing substrates to 6-amino-6-deoxyglucose.
(SEQ ID NO: 2)

YALPMTGK (SEQ ID NO: 2) was used as a potential sortase substrate. A 1:1 mixture of the peptide and the 6-amino-6-deoxyglucose sugar was incubated with and without sortase for 4 to 6 hours subsequent to which the reaction mixture was analyzed by reverse-phase high performance liquid chromatography (RPHPLC) and other methods known in the art. The RPHPLC chromatographic profile of the sample that contained sortase revealed two new peaks as compared with the control sample (without sortase). The electrospray mass spectrometric (ESMS) analyses of the new peaks were in accordance with the calculated mass of YALPMT (SEQ ID NO: 9) or an YALPMT (SEQ ID NO: 9)-sugar adduct suggesting that the above amino sugar could indeed act as a nucleophile in the transamidation reaction catalyzed by sortase. The reaction scheme is as shown below.

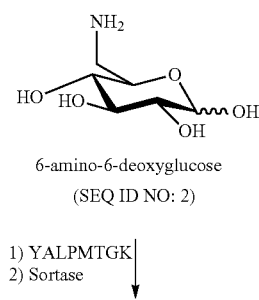

6-amino-6-deoxyglucose
(SEQ ID NO: 2)

1) YALPMTGK
2) Sortase

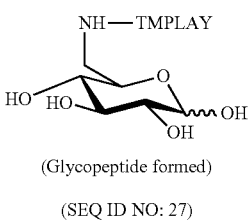

(Glycopeptide formed)

(SEQ ID NO: 27)

However, the formation of the amide bond between the Threonyl carboxyl of an LPXTG (SEQ ID NO: 11) motif and the amino sugar, 2-amino-2-deoxyglucose (glucosamine), by the same mechanism was not observed (as shown in the reaction scheme below).

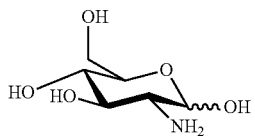

2-amino-2-deoxyglucose
(glucosamine)
(SEQ ID NO: 2)

1) YALPMTGK
2) Sortase

No Glycopeptide formed

It was then explored if 6-amino-6-deoxyhexopyranose could be recognized by sortase when this moiety is present in the context of a larger molecule. For this the ligation of two peptides namely, YALPMTGK (SEQ ID NO: 2) and RRRRRRRRRLPMTGK (SEQ ID NO: 4), with aminoglycoside antibiotics such as

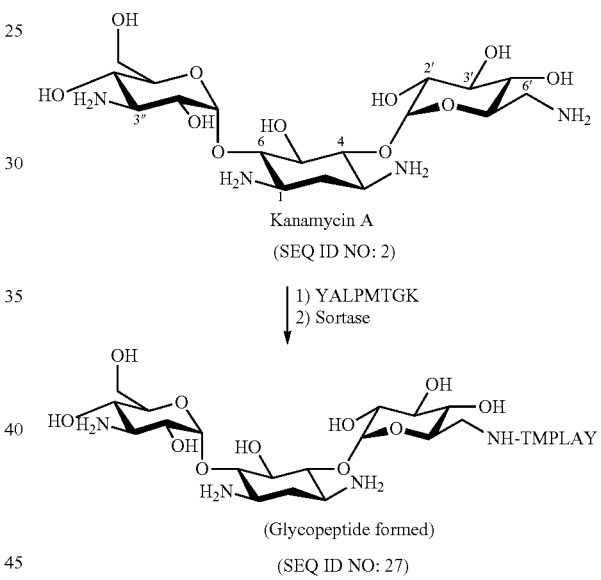

kanamycin, tobramycin, paramomycin, ribostamycin and neomycin was tested. A representative reaction scheme is shown above (one OH group was missing in the structure, that now appears in Times NEW ROMAN). The coupling of each of the peptides with the individual antibiotics was carried out for 4 to 6 hours at 37° C. in the presence of sortase. The RPHPLC of the reaction mixture followed by ESMS analyses of the product indeed confirmed the formation of the expected peptide-antibiotic conjugate in each case. Details of the ESI mass analyses of synthetic peptides used in sortase-mediated ligation reactions are provided in Table 1.

The processes used for the same are described in the examples. The electro-spray mass results and the theoretically expected results for the products are also tabulated. The values clearly indicate that the products obtained were the expected bioconjugates. Thus, it was demonstrated that sortase-catalyzed transamidation reaction can be utilized for constructing therapeutic bioconjugates consisting of relevant peptides and molecules containing a 6-amino-6-deoxyhexopyranose moiety.

Figure 3:
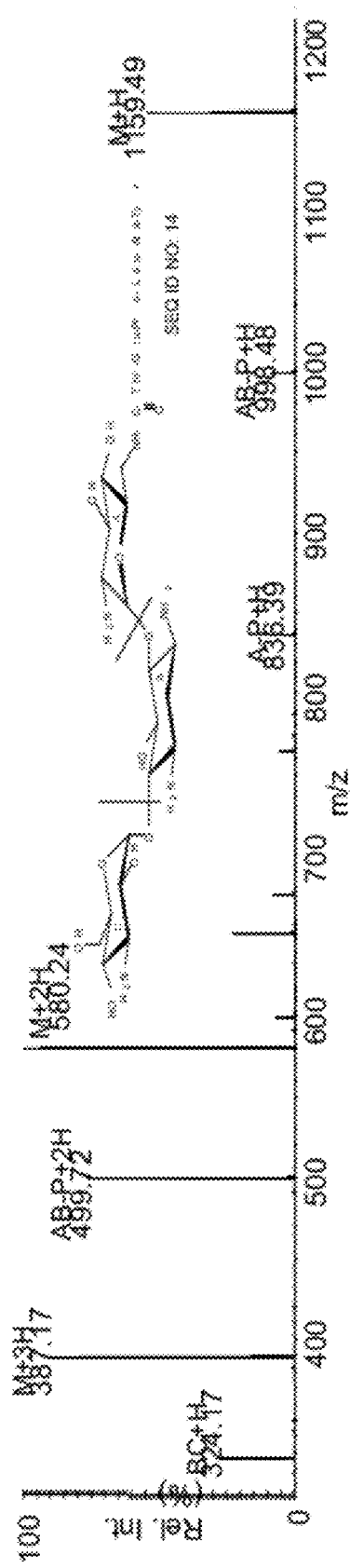
FIG. 3 shows ESI mass spectrometric characterization of kanamycin A conjugate.
Figure 4:
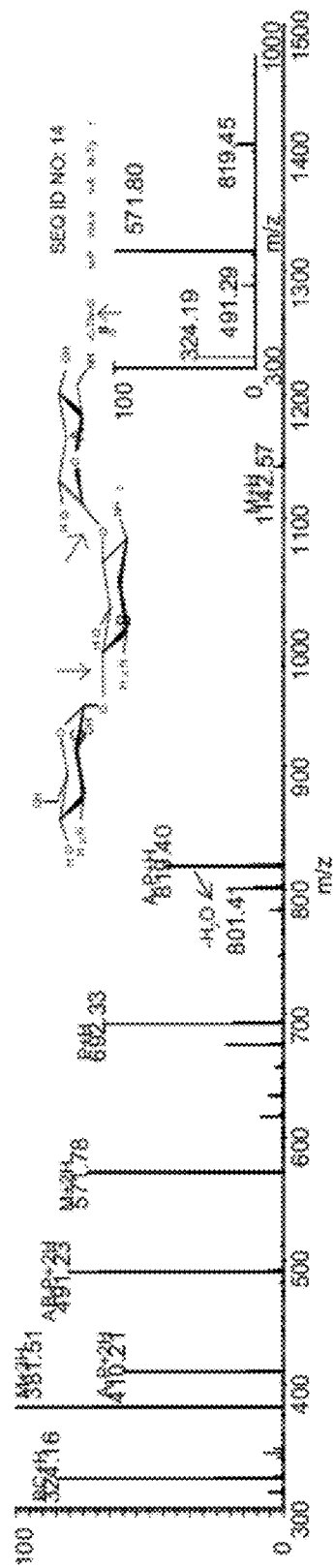
FIG. 4 shows ESI mass spectrometric characterization of tobramycin conjugate.

The conjugation of YALPETGK (SEQ ID NO: 1) peptide substrate to several antibiotics was also tested. RPHPLC analyses of the each reaction mixture containing respective antibiotics and YALPETGK (SEQ ID NO: 1) peptide substrate in the presence of sortase yielded a new product peak (indicated by an arrow in FIG. 2A) besides the hydrolyzed peptide substrate. The yields of the conjugates varied from 35% for kanamycin A and B, and about 70% for tobramycin. ESMS was carried out to delineate the site of peptide attachment in the antibiotics substrate. The presence of m/z 836.4 in kanamycin A (FIG. 3) The three rings of the antibiotics structure are labeled as A, B and C, and the peptide portion is designated as P. The ions carry the labels based on the part of the structure from which they are derived. For example, m/z 836.39 labeled as A-P represents a structure in which ring A is attached to the peptide; m/z 835.4 in kanamycin B and m/z 819.4 in tobramycin (FIG. 4) unequivocally showed occurrence of peptide ligation exclusively in the ring A at the 6-amino site in these antibiotics.

Figure 2:
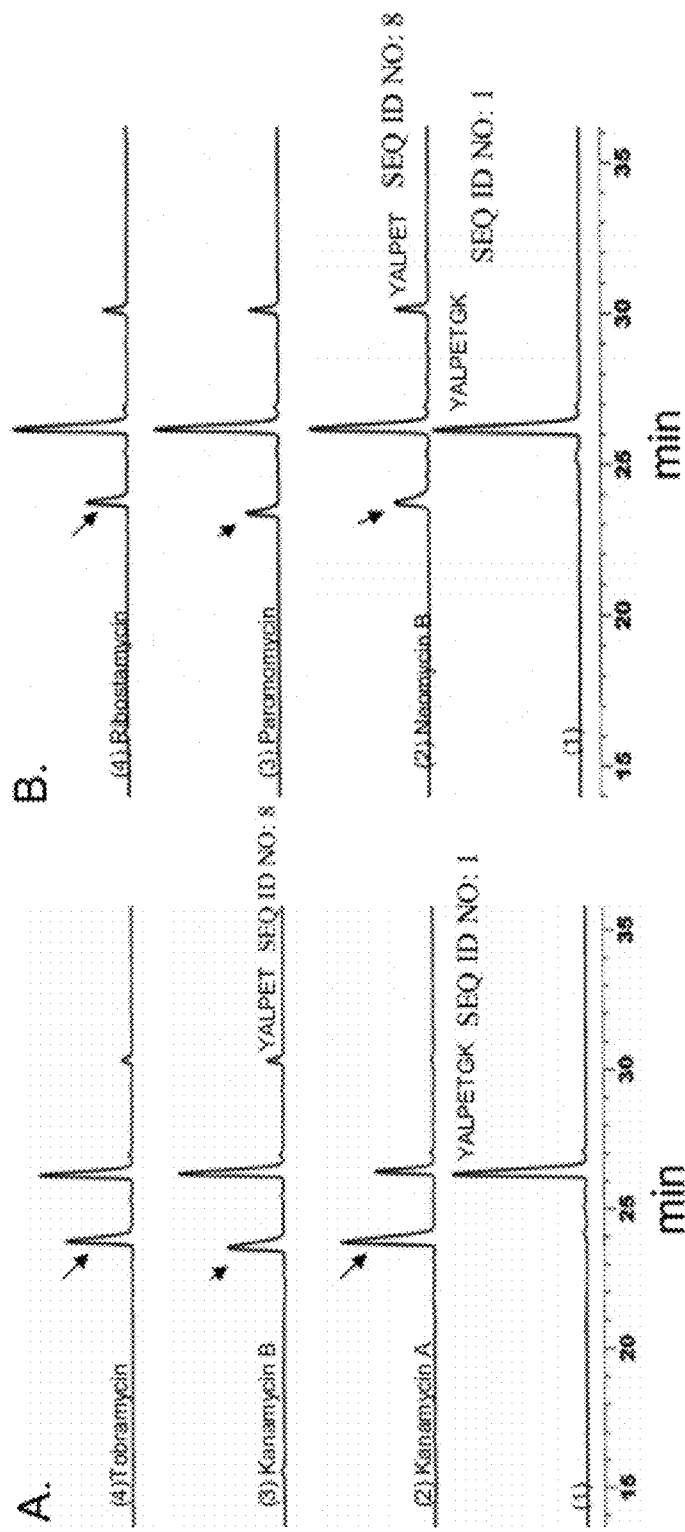
FIG. 2 shows RPHPLC analyses of sortase-catalyzed conjugation of YALPETGK (SEQ ID NO. 1) to antibiotics.
Figure 5:
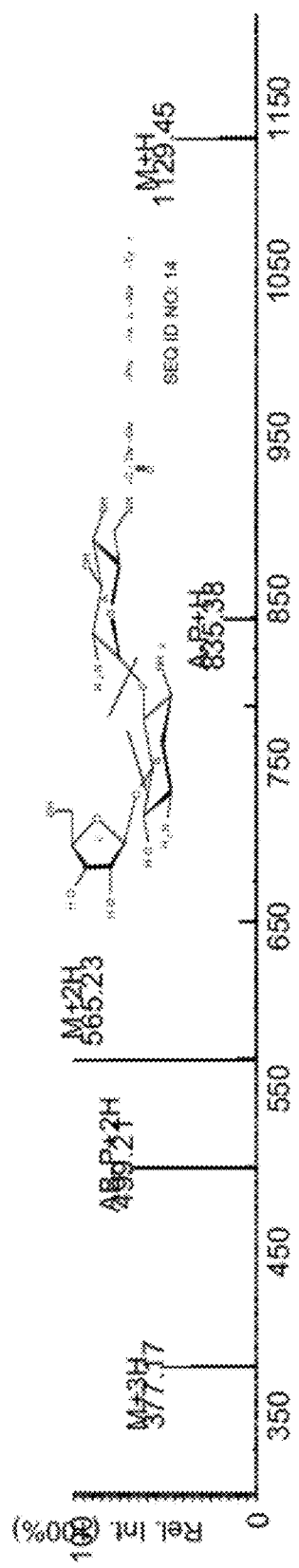
FIG. 5 shows ESI mass spectrometric characterization of ribostamycin conjugate.
Figure 6:
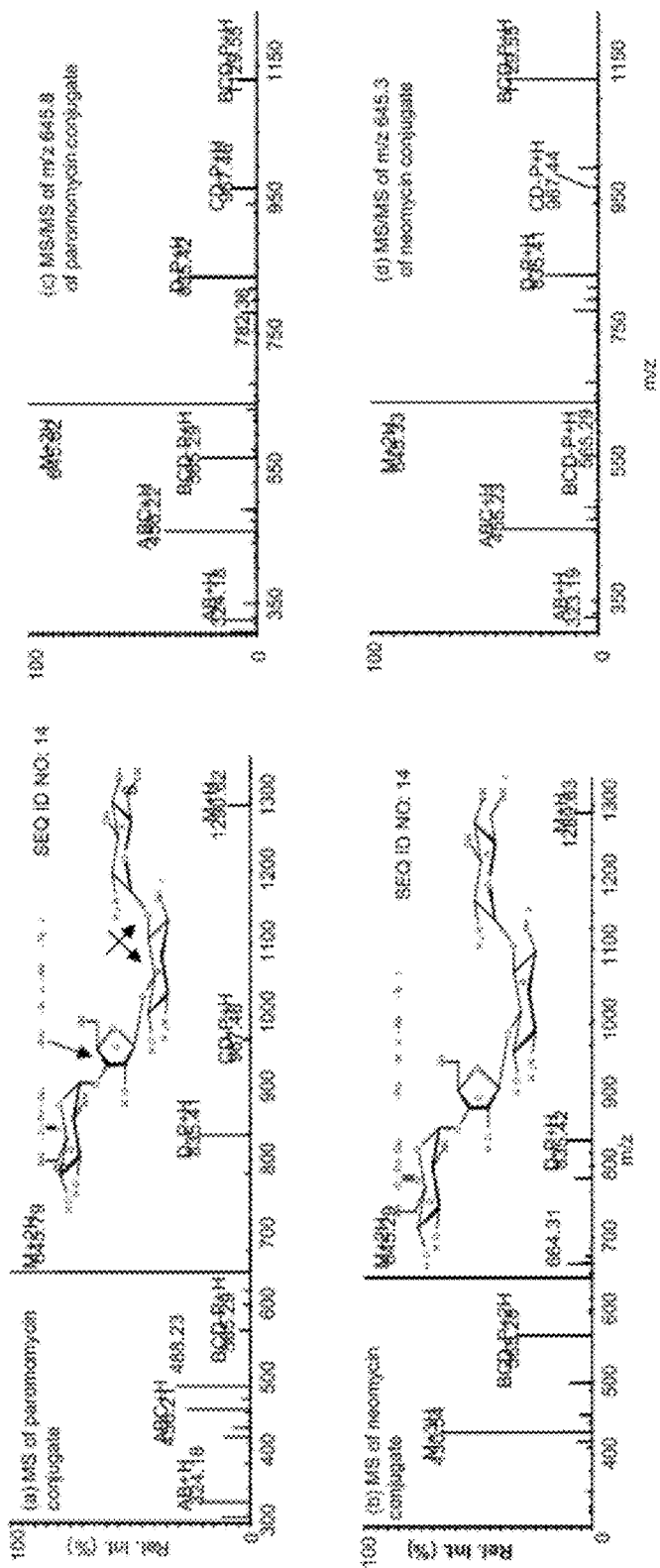
FIG. 6 shows ESI mass spectrometric characterization of paramomycin conjugate and neomycin B conjugate.

A single peptide-antibiotics conjugate peak was obtained in RPHPLC analyses when YALPETGK (SEQ ID NO: 1) was used as a peptide substrate in the presence of sortase and the respective antibiotics (FIG. 2 B). The yield of the product for these antibiotics was in the range of 20-30%. ESMS analyses showed that the 6-amino group of ring A was also the site of ligation (m/z 835.4) in the case ribostamycin (FIG. 5). However, ESMS fragmentation pattern of paromomycin and neomycin conjugates (m/z 967.4) showed that sortase-mediated peptide ligation occurred at the 6-amino site in the D-ring of these antibiotics (FIGS. 6A and 6B). This was corroborated by the MS/MS spectra of doubly charged species (shown in FIGS. 6C and 6D) of the respective conjugate. The results show that the 6-amino site in the ring A of neomycin B was refractory to sortase-catalyzed peptide ligation.

Cells take up Polyarginine sequences very efficiently. Therefore, polyarginine containing aminoglycoside antibiotics such as but not limited to (R)$_9$LPMT (SEQ ID NO: 15)-Tobramycin, (R)$_9$LPMT (SEQ ID NO: 15)-Neomycin, (R)$_9$LPMT (SEQ ID NO: 15)-Ribostamycin etc, are likely to be taken up by cells more efficiently and be more bio-effective. These [(R)$_9$LPMT (SEQ ID NO: 15)—Tobramycin, (R)$_9$LPMT (SEQ ID NO: 15)-Neomycin, (R)$_9$LPMT (SEQ ID NO: 15)-Ribostamycin etc] or similar conjugates may also elicit anti-HIV activity by interfering with the Tat-TAR and Rev-RRE interactions.

Tat and Rev are two essential regulatory proteins that play important roles in HIV replication. Both Tat and Rev act through structured viral RNA target sites, TAR in the case of Tat and RRE in the case of Rev. Short arginine rich peptide sequences derived from Tat and Rev have been shown to mimic the action of respective parent proteins. Besides, a nonaarginine peptide (R$_9$) is known to bind to TAR with the same affinity and specificity as the wild type Tat peptide. Since aminoglycoside antibiotics also bind to TAR and RRE RNA, the bio-conjugates of the type mentioned above are likely to be potent inhibitors of HIV replication.

Table 2 provides some examples of the various synthetic bioconjugates that are produced using sortase.

One embodiment of the present disclosure provides a novel therapeutic and/or diagnostic bioconjugate useful for target delivery of a compound, wherein the bioconjugate comprises a substrate comprising LPXTG (SEQ ID NO: 11) peptide motif capable of recognizing sortase, wherein said substrate is selected from a group consisting of peptides, polypeptides, proteins, glycoprotein, lipoprotein, antibodies, radionucleotides, fluorophores, ligand chromophore and any compound comprising the LPXTG peptide motif and a biomolecule selected from a group consisting of aminoglycoside, polyamines, aminosugars, hydroxyamino acids, hydroxyamino acid esters, aminolipids and any other compound comprising these moieties.

Another embodiment of the present disclosure provides a novel therapeutic and/or diagnostic bioconjugate useful for target delivery of a compound, wherein the substrate is covalently linked to the biomolecule by a sortase catalyzed ligation mechanism.

In one embodiment of the present invention a peptide is used as the substrate for the preparation of the bioconjugates wherein the amino acid sequence of the peptide is as set forth in SEQ ID NO: 1 or SEQ ID NO: 2 or SEQ ID NO: 3 or SEQ ID NO: 4 or SEQ ID NO: 5 or a variant thereof.

Still another embodiment of the present disclosure relates to various aminoglycosides such as ribostamycin, butirosin, paromomycin, neomycin, lividomycin, kanamycin, tobramycin, dibekacin, gentamicin, sismocin, netilimicin, isepamicin, arbekacin, amikacin, streptomycin, apramycin, hygromycin, neamine, vancomycin and kasugamycin used in the preparation of the bioconjugate disclosed in the present invention.

Still yet another embodiment of the present disclosure provides a novel therapeutic and diagnostic bioconjugate useful for target delivery of a compound, wherein the aminosugar is selected from a group consisting of 6-amino-6-deoxyglucose, 6-amino-6-deoxymannose, 6-amino-6-deoxyallose, 6-amino-6-deoxyaltrose, 6-amino-6-deoxyidose, 6-amino-6-deoxygalactose and 6-amino-6-deoxytalose.

Further embodiment of the present disclosure provides a novel therapeutic and diagnostic bioconjugate useful for target delivery of a compound, wherein the polyamine is selected from a group consisting of spermine, spermidine and agmatine.

Yet another embodiment of the present disclosure provides a novel therapeutic and diagnostic bioconjugate useful for target delivery of a compound, wherein the hydroxy amino acid is selected from a group consisting of 4-amino-3-hydroxybutyric acid, 4-amino-2-hydroxybutyric acid and etahnolamine.

Still another embodiment of the present disclosure provides a novel therapeutic and diagnostic bioconjugate useful for target delivery of a compound, wherein the hydroxy amino acid ester is selected from a group consisting of 4-amino-3-hydroxybutyryl stearate, 4-amino-3-hydroxybutyryl palmitate, 4-amino-3-hydroxybutyryl acetate, 4-amino-3-hydroxybutyryl propionate, butyrate/or 4-amino-2-hydroxybutyryl-acetate, 4-amino-2-hydroxybutyryl-propionate, 4-amino-2-hydroxybutyryl-butyrate, 4-amino-2-hydroxybutyryl-stearate, 4-amino-2-hydroxybutyrylpalmitate, 4-amino-2-hydroxy-butyryl-coenzyme A, 4-amino-3-hydroxybutyrylpalmitate, 4-amino-2-hydroxybutyryl-coenzyme A.

Still yet another embodiment of the present disclosure provide a novel therapeutic and diagnostic bioconjugate useful for target delivery of a compound, wherein the amino lipid is N-[(3-hexadecanoyloxy)hexadecanoyl]ornithine or virodhamine.

Further embodiment of the present disclosure provides a process of preparing the bioconjugate, said process comprising:
a. providing a substrate comprising LPXTG (SEQ ID NO: 11) peptide motif capable of recognizing sortase, wherein said substrate is selected from a group consisting of peptides, polypeptides, proteins, glycoprotein, lipoprotein, antibodies, radionucleotides, fluorophores, ligand, chromophore and any compound comprising the LPXTG (SEQ ID NO: 11) peptide motif;

b. providing a biomolecule selected from a group consisting of aminoglycoside, hexopyranose, polyamines, aminosugars, hydroxyamino acids, hydroxyamino acid esters, aminolipids and any compound comprising these moieties;

c. providing sortase to catalyze the ligation reaction of said substrate and said biomolecule under suitable conditions to obtain said bioconjugate Another embodiment of the present disclosure provides a process of preparing the bioconjugate, wherein the sortase is isolated from *Staphylococcus aureus*.

Yet another embodiment of the present disclosure provides a substrate in the form of a peptide comprising an amino acid sequence as set forth in SEQ ID NO: 1 or SEQ ID NO: 2 or SEQ ID NO: 3 or SEQ ID NO: 4 or SEQ ID NO: 5 or a variant thereof.

Still yet another embodiment of the present disclosure provides aminoglycoside such as ribostamycin, butirosin, paromomycin, neomycin, lividomycin, kanamycin, tobramycin, dibekacin, gentamicin, sismocin, netilimicin, isepamicin, arbekacin and amikacin.

In one embodiment the aminosugar is selected from a group consisting of 6-amino-6-deoxyglucose, 6-amino-6-deoxymannose, 6-amino-6-deoxyallose, 6-amino-6-deoxyaltrose, 6-amino-6-deoxyidose, 6-amino-6-deoxygalactose and 6-amino-6-deoxytalose.

Yet another embodiment of the present disclosure provides a process of preparing the bioconjugate, wherein the polyamine is selected from a group consisting of spermine, spermidine and agmatine.

Still another embodiment of the present disclosure provides a process of preparing the bioconjugate, wherein the hydroxyamino acid is selected from a group consisting of 4-amino-3-hydroxybutyric acid, 4-amino-2-hydroxybutyric acid and ethanolamine.

Another embodiment of the present disclosure provides a composition useful as therapeutic or diagnostic agent comprising the bioconjugate and pharmaceutically acceptable salts thereof.

Further embodiment of the present disclosure provides a kit useful for therapy or diagnosis comprising said bioconjugate and reagents suitable for administering said bioconjugate to an individual.

One embodiment of the present disclosure provides a method of detection of a ligand or a compound that binds to the bioconjugate disclosed in the present invention.

One embodiment of the present disclosure provides a method for cloning, expression and purification of recombinant sortase. Detailed procedure is described in Example 1.

Another embodiment of the present disclosure provides a method for the synthesis of peptides. For details refer Example 2.

Yet another embodiment of the present disclosure provides Sortase-catalyzed peptide ligation reaction. The ligation of various LPXTG (SEQ ID NO: 11) containing peptides and sugar or aminoglycoside antibiotics is described (Example 3).

Still another embodiment of the present disclosure provides Sortase-catalyzed ligation of model peptides to aminosugars. Sortase ligated LPXTG (SEQ ID NO: 11) containing substrates to aminosugar such as 6-amino-6-deoxyglucose but not to 2-amino-2-deoxyglucose glucosamine (Example 4).

Still yet another embodiment of the present disclosure provides a Sortase-catalyzed ligation of peptides to aminoglycoside antibiotics. The ability of sortase was tested to ligate peptides to aminoglycoside class of therapeutically important antibiotics that are built up by a variety of aminosugars of the 6-amino or the 2,6-diamino type besides containing several other amino functionalities. Details are provided in Example 5.

One embodiment of the present disclosure provides a process for preparation of bioconjugate by sortase catalyzed ligation reaction using YALPMTGK (SEQ ID NO: 2) peptide and Kanamycin B antibiotic. For details refer Example 6.

Another embodiment of the present disclosure provides a process for preparation of bioconjugate by sortase catalyzed ligation reaction using YALPMTGK (SEQ ID NO: 2) peptide and Tobramycin antibiotic. For details refer Example 7.

Yet another embodiment of the present disclosure provides a process for preparation of bioconjugate by sortase catalyzed ligation reaction using YALPMTGK (SEQ ID NO: 2) peptide and Paromomycin antibiotic. For details refer Example 8.

Still another embodiment of the present disclosure provides a process for preparation of bioconjugate by sortase catalyzed ligation reaction using YALPMTGK (SEQ ID NO: 2) peptide and Ribostamycin antibiotic. For details refer Example 9.

Still yet another embodiment of the present disclosure provides a process for preparation of bioconjugate by sortase catalyzed ligation reaction using YALPMTGK (SEQ ID NO: 2) peptide and Neomycin antibiotic. For details refer Example 10.

One embodiment of the present disclosure provides a process for preparation of bioconjugate by sortase catalyzed ligation reaction using $(R)_9$LPMTGK (SEQ ID NO: 4) peptide and Kanamycin B antibiotic. For details refer Example 11.

Another embodiment of the present disclosure provides a process for preparation of bioconjugate by sortase catalyzed ligation reaction using $(R)_9$LPMTGK (SEQ ID NO: 4) peptide and Tobramycin antibiotic. For details refer Example 12.

Yet another embodiment of the present disclosure provides a process for preparation of bioconjugate by sortase catalyzed ligation reaction using $(R)_9$LPMTGK (SEQ ID NO:4) peptide and Paromomycin antibiotic. For details refer Example 13.

Still another embodiment of the present disclosure provides a process for preparation of bioconjugate by sortase catalyzed ligation reaction using $(R)_9$LPMTGK (SEQ ID NO: 4) peptide and Ribostamycin antibiotic. For details refer Example 14.

Still yet another embodiment of the present disclosure provides a process for preparation of bioconjugate by sortase catalyzed ligation reaction using Tat and Rev mimetics to antibiotics. Ligation of peptides derived from Tat and Rev protein of HIV to aminoglycoside antibiotics was considered. Tat and Rev are two essential regulatory proteins that play important roles in HIV replication. For details refer Example 15.

One embodiment of the present disclosure provides a method of peptide ligation to amikacin and butirosin A. For details refer Example 16.

Another embodiment of the present disclosure provides a method of Sortase-catalyzed peptide ligation to polyamine spermine. For details refer Example 17.

While particular embodiments of the subject invention have been described, it will be obvious to those skilled in the art that various changes and modifications of the subject invention can be made without departing from the spirit and scope of the invention. In addition, while the present invention has been described in connection with certain specific

EXAMPLES

The following examples are put forth so as to provide those of ordinary skill in the art with a complete disclosure and the description of how to make and use the present invention, and are not intended to limit the scope of what the inventors regard as their invention nor are they intended to represent that the experiments below are all and only experiments performed.

Example 1

Cloning, Expression and Purification of Recombinant Sortase

The forward primer (SEQ ID NO: 6) and reverse primer (SEQ ID NO: 7) were used to amplify the $SrtA_{A59}$ sequence corresponding to amino acids 60-204 from the genomic DNA of *Staphylococcus aureus* Mu50 strain.

```
                                            SEQ ID NO: 6
FP 5'-GATATACATATGCAAGCTAAACCTCAAATTCCG-3'

SEQ ID NO: 7
RP5'-GTGGTGCTCGAGTTTGACTTCTGTAGCTACAAAGAT-3'
```

The resulting amplicon was ligated into pGEM-T Easy vector, transformed into *Escherichia coli* (*E. coli*) XL-I Blue competent cells and selected from Luria-Bertani (LB) agar plates containing 50 μg/ml ampicillin. The selected clones were verified by DNA sequencing for the presence of the desired construct. Plasmid DNA isolated from the positive clones was digested with NdeI and XhoI and ligated into pET23b vector for expressing a recombinant sortase with a C-terminal hexa-histidine tag. The ligation mixture was transformed into *E. coli* XLI Blue competent cells and selected from 50 μg/ml ampicillin containing LB agar plates. Plasmid DNA isolated from the positive clones was used to transform *E. coli* BL21 (DE3) competent cells. The transformed clones were propagated in LB broth at 37° C. for 3 hours or till the $OD_{600}$ reached 0.6 and the expression was induced by addition of IPTG to a final concentration of 0.2 mM, at 30° C. for 3 hours. The induced cells were pelleted, resuspended in 10 mM Tris-HCl, pH 7.5, 50 mM NaCl, 1 mM 2-mercaptoethanol (β-ME) and lysed by sonication. The protein in the lysate supernatant was purified by Ni-NTA affinity chromatography. The purified protein was freed of excess imidazole using a 10DG desalting column. The identity of recombinant sortase ($SrtA_{A59}$) was established by Electrospray (ES) mass spectrometry (MS). The experimental mass (17864.78 Da) was in agreement with the calculated value (17865 Da). Other methods well known in the art can also be used.

Example 2

Synthesis of Peptides

The peptides were synthesized by standard solid phase synthesis protocols using Fmoc chemistry on a semi-automated peptide synthesizer. Wang resin preloaded with the desired amino acid was used as the starting material. The coupling and deprotection was monitored at every step by the Kaiser test for free amines. Before each coupling step and on completion of the synthesis, the N-terminal Fmoc group was removed using 20% piperidine (v/v in DMF). The peptides were cleaved from the resin and the side chains deprotected with a mixture containing trifluoro acetic acid (TFA), ethanediol, phenol, thioanisole and water (80:5:5:5:5, v/v). The resin was removed by filtration and the crude peptides were precipitated using cold diethyl ether. The peptides were purified to ≧98% by RPHPLC, lyophilized and stored at −70° C. The chemical identity of the peptides was checked by mass spectrometry. Other methods well known in the art may be used for the synthesis of peptides or polypeptides or proteins.

Example 3

Sortase-Catalyzed Peptide Ligation Reaction

The ligation of various substrate comprising LPXTG (SEQ ID NO: 11) peptide motif capable of recognizing sortase with biomolecule such as aminoglycoside, hexopyranose, polyamines, aminosugars, hydroxyamino acids, hydroxyamino acid esters, aminolipids and any other compound comprising these moieties was carried out in 0.3M Tris-acetate buffer (pH 7.5) containing 150 mM Nacl, 5 mM $CaCl_2$, and 2 mM 2-mercaptoethanol. Each assay was set up in a 0.1 ml volume that contained 0.5 mM peptide, 1 mM sugar or antibiotics and 50 μM sortase. The reaction was allowed to proceed at 37° C. for 4-6 hours, quenched by addition of 20-fold excess of 0.1% trifluoroacetic acid (TFA) and analyzed by RPHPLC using acetonitrile-water-TFA solvent system. The reaction products were characterized by ESMS and/or MALDI-TOF mass spectrometry.

Example 4

Soratse-Catalyzed Ligation of Model Peptides or Polypeptides to Aminosugars

Sortase was ligated to two model substrates containing LPXTG (SEQ ID NO: 11) motif, YALPETGK (SEQ ID NO: 1) and YALPMTGK (SEQ ID NO: 2) with aminosugar, namely, 6-amino-6-deoxyglucose. However, other peptides or polypeptides and sugar substrates well known in the art can similarly be used. The peptide YALPMTGK (SEQ ID NO: 2) and the sugar, 6-amino-6-deoxyglucopyranose (adg) were taken in 0.05M Tris-acetate buffer (pH 7.5) (containing 150 mM Nacl, 5 mM $Cacl_2$, and 2 mM 2-mercaptoethanol) and incubated with sortase at about 37° C. for about 4-6 hours. The reaction was quenched by addition of 20 to 40-fold excess of 0.1% trifluoroacetic acid (TFA). The reaction mixture was analyzed by RPHPLC using acetonitrile-water-TFA solvent system. Reaction products obtained from RPHPLC were characterized by ESMS. The observed mass of the reaction product was 856.62 Da and the expected theoretical mass of YALPMT (SEQ ID NO: 9)-adg conjugate was 856.07 Da. The RPHPLC of the reaction mixture followed by ESMS analyses of the product indeed confirmed the formation of the expected peptide-sugar conjugate (Refer table 2).

The chromatographic profile of the sample that contained 6-amino-6-deoxyglucose and YALPETGK (SEQ ID NO: 1) revealed two new peaks [FIG. 1A (a), 0 h control; (b), 6 h reaction with glucosamine; (c), 6 h reaction with 6-deoxy-6-aminoglucopyranose, FIG. 1 B) ESI-MS of the product (indicated by an arrow in c) isolated from RPHPLC.] Electrospray mass spectrometric analyses (Table 2) of the new peaks were in accordance with the calculated mass of YALPET (SEQ ID NO: 16) (hydrolysed product) or a sugar-TEPLAY (SEQ ID NO: 14) adduct suggesting that the above amino sugar indeed acted as a nucleophile in the transamidation reaction catalyzed by sortase. The ligation reaction with the above peptides proceeded in much the same way when 6-amino-6-deoxymannose was used an aminosugar.

Similarly a substrate containing (2-amino-2-deoxyglucose) glucosamine was ligated with either YALPETGK (SEQ ID NO: 1) or YALPMTGK (SEQ ID NO: 2). RPHPLC profile of this reaction revealed that the substrate peptide was hydrolyzed to YALPET (SEQ ID NO: 16) without the formation of an adduct.

Example 5

Sortase-Catalyzed Ligation of Peptides or Polypeptides to Aminoglycoside Antibiotics The ability of sortase was tested to ligate peptides or polypeptides to aminoglycoside class of therapeutically important antibiotics that are built up by a variety of aminosugars of the 6-amino or the 2,6-diamino type besides containing several other amino functionalities. The central scaffold of aminoglycoside antibiotics is the 2-deoxystreptamine ring to which aminosugars are substituted at positions 4 and 6 (as in tobramycin and kanamycin) or 4 and 5 (as in ribostamycin, neomycin and paramomycin). The sortase-mediated conjugation of the aminoglycoside antibiotics with YALPETGK (SEQ ID NO: 1) or YALPMTGK (SEQ ID NO: 2) model peptide substrates was tested. Other sequences like SEQ ID NO: 3, SEQ ID NO: 4 and SEQ ID NO: 5 or any polypeptide containing LPXTG (SEQ ID NO: 11) sequence motif can be similarly used.

Example 6

Synthesis of Sortase Catalyzed Ligation Product Formed from YALPMTGK (SEQ ID NO: 2) Peptide and Kanamycin B Antibiotic The peptide YALPMTGK (SEQ ID NO:2) and the antibiotic, Kanamycin B, were taken in 0.05M Tris-acetate buffer (pH 7.5) (containing 150 mM NaCl, 5 mM $CaCl_2$, and 2 mM 2-mercaptoethanol) and incubated with sortase at 37° C. for 4-6 hours. The reaction was quenched by addition of 20 to 40-fold excess of 0.1% trifluoroacetic acid (TFA). The reaction mixture was analyzed by RPHPLC using acetonitrile-water-TFA solvent system. Reaction products obtained from RPHPLC were characterized by ESMS. The observed mass of the reaction product was 1159.93 Da and the expected theoretical mass of YALPMT (SEQ ID NO: 9)-Kanamycin B conjugate was 1160.9 Da. The RPHPLC of the reaction mixture followed by ESMS analyses of the product indeed confirmed the formation of the expected peptide-antibiotic conjugate. (Refer table 2).

Example 7

Synthesis of Sortase Catalyzed Ligation Product Formed from YALPMTGK (SEQ ID NO: 2) Peptide and Tobramycin Antibiotic The peptide YALPMTGK (SEQ ID NO:2) and the antibiotic, Tobramycin, were taken in 0.05M Tris-acetate buffer (pH 7.5) (containing 150 mM NaCl, 5 mM $CaCl_2$, and 2 mM 2-mercaptoethanol) and incubated with sortase at 37° C. for 4-6 hours. The reaction was quenched by addition of 20 to 40-fold excess of 0.1% trifluoroacetic acid (TFA). The reaction mixture was analyzed by RPHPLC using acetonitrile-water-TFA solvent system. Reaction products obtained from RPHPLC were characterized by ESMS. The observed mass of the reaction product was 1144.03 Da and the expected theoretical mass of YALPMT (SEQ ID NO: 9)—Tobramycin conjugate was 1144.5 Da. The RPHPLC of the reaction mixture followed by ESMS analyses of the product indeed confirmed the formation of the expected peptide-antibiotic conjugate. (Refer table 2).

Example 8

Synthesis of Sortase Catalyzed Ligation Product Formed from YALPMTGK (SEQ ID NO: 2) Peptide and Paromomycin Antibiotic The peptide YALPMTGK (SEQ ID NO:2) and the antibiotic, Paromomycin, were taken in 0.05M Tris-acetate buffer (pH 7.5) (containing 150 mM NaCl, 5 mM $CaCl_2$, and 2 mM 2-mercaptoethanol) and incubated with sortase at 37° C. for 4-6 hours. The reaction was quenched by addition of 20 to 40-fold excess of 0.1% trifluoroacetic acid (TFA). The reaction mixture was analyzed by RPHPLC using acetonitrile-water-TFA solvent system. Reaction products obtained from RPHPLC were characterized by ESMS. The observed mass of the reaction product was 1292.09 Da and the expected theoretical mass of YALPMT (SEQ ID NO: 9)—Paromomycin conjugate was 1292.6 Da. The RPHPLC of the reaction mixture followed by ESMS analyses of the product indeed confirmed the formation of the expected peptide-antibiotic conjugate. (Refer table 2).

Example 9

Synthesis of Sortase Catalyzed Ligation Product Formed from YALPMTGK (SEQ ID NO: 2) Peptide and Ribostamycin Antibiotic The peptide YALPMTGK (SEQ ID NO:2) and the antibiotic, Ribostamycin, were taken in 0.05M Tris-acetate buffer (pH 7.5) (containing 150 mM NaCl, 5 mM $CaCl_2$, and 2 mM 2-mercaptoethanol) and incubated with sortase at 37° C. for 4-6 hours. The reaction was quenched by addition of 20 to 40-fold excess of 0.1% trifluoroacetic acid (TFA). The reaction mixture was analyzed by RPHPLC using acetonitrile-water-TFA solvent system. Reaction products obtained from RPHPLC were characterized by ESMS. The observed mass of the reaction product was 1130.86 Da and the expected theoretical mass of YALPMT (SEQ ID NO: 9)—Ribostamycin conjugate was 1131.5 Da. The RPHPLC of the reaction mixture followed by ESMS analyses of the product indeed confirmed the formation of the expected peptide-antibiotic conjugate. (Refer table 2).

Example 10

Synthesis of Sortase Catalyzed Ligation Product Formed from YALPMTGK (SEQ ID NO: 2) Peptide and Neomycin Antibiotic The peptide YALPMTGK (SEQ ID NO:2) and the antibiotic, Neomycin, were taken in 0.05M Tris-acetate buffer (pH 7.5) (containing 150 mM NaCl, 5 mM $CaCl_2$, and 2 mM 2-mercaptoethanol) and incubated with sortase at 37° C. for 4-6 hours. The reaction was quenched by addition of 20 to 40-fold excess of 0.1% trifluoroacetic acid (TFA). The reaction mixture was analyzed by RPHPLC using acetonitrile-water-TFA solvent system. Reaction products obtained from RPHPLC were characterized by ESMS. The observed mass of the reaction product was 1193.47 Da and the expected theoretical mass of YALPMT (SEQ ID NO: 9)—Neomycin conjugate was 1194.3 Da. The RPHPLC of the reaction mixture followed by ESMS analyses of the product indeed confirmed the formation of the expected peptide-antibiotic conjugate. (Refer table 2).

Example 11

Synthesis of Sortase Catalyzed Ligation Product Formed from (R)$_9$LPMTGK (SEQ ID NO: 4) Peptide and Kanamycin B Antibiotic The peptide (R)$_9$LPMTGK (SEQ ID NO: 4) and the antibiotic, Kanamycin B, were taken in 0.05M Tris-acetate buffer (pH 7.5) (containing 150 mM NaCl, 5 mM CaCl$_2$, and 2 mM 2-mercaptoethanol) and incubated with sortase at 37° C. for 4-6 hours. The reaction was quenched by addition of 20 to 40-fold excess of 0.1% trifluoroacetic acid (TFA). The reaction mixture was analyzed by RPHPLC using acetonitrile-water-TFA solvent system. Reaction products obtained from RPHPLC were characterized by ESMS. The observed mass of the reaction product was 2331.8 Da and the expected theoretical mass of (R)$_9$LPMT (SEQ ID NO: 15)—Kanamycin B conjugate was 2331.63 Da. The RPHPLC of the reaction mixture followed by ESMS analyses of the product indeed confirmed the formation of the expected peptide-antibiotic conjugate. (Refer table 2).

Example 12

Synthesis of Sortase Catalyzed Ligation Product Formed from (R)$_9$LPMTGK (SEQ ID NO:4) Peptide and Tobramycin Antibiotic The peptide (R)$_9$LPMTGK (SEQ ID NO:4) and the antibiotic, Tobramycin, were taken in 0.05M Tris-acetate buffer (pH 7.5) (containing 150 mM NaCl, 5 mM CaCl$_2$, and 2 mM 2-mercaptoethanol) and incubated with sortase at about 37° C. for about 4-6 hours. The reaction was quenched by addition of 20 to 40-fold excess of 0.1% trifluoroacetic acid (TFA). The reaction mixture was analyzed by RPHPLC using acetonitrile-water-TFA solvent system. Reaction products obtained from RPHPLC were characterized by ESMS. The observed mass of the reaction product was 2315.9 Da and the expected theoretical mass of (R)$_9$LPMT—Tobramycin conjugate was 2315.5 Da. The RPHPLC of the reaction mixture followed by ESMS analyses of the product indeed confirmed the formation of the expected peptide-antibiotic conjugate (Refer table 2).

Example 13

Synthesis of Sortase Catalyzed Ligation Product Formed from (R)$_9$LPMTGK (SEQ ID NO:4) Peptide and Paromomycin Antibiotic The peptide (R)$_9$LPMTGK (SEQ ID NO: 4) and the antibiotic, Paromomycin, were taken in 0.05M Tris-acetate buffer (pH 7.5) (containing 150 mM NaCl, 5 mM CaCl$_2$, and 2 mM 2-mercaptoethanol) and incubated with sortase at about 37° C. for about 4-6 hours. The reaction was quenched by addition of 20 to 40-fold excess of 0.1% trifluoroacetic acid (TFA). The reaction mixture was analyzed by RPHPLC using acetonitrile-water-TFA solvent system. Reaction products obtained from RPHPLC were characterized by ESMS. The observed mass of the reaction product was 2463.17 Da and the expected theoretical mass of (R)$_9$LPMT (SEQ ID NO: 15)—Paromomycin conjugate was 2463.63 Da. The RPHPLC of the reaction mixture followed by ESMS analyses of the product indeed confirmed the formation of the expected peptide-antibiotic conjugate (Refer table 2).

Example 14

Synthesis of Sortase Catalyzed Ligation Product Formed from (R)$_9$LPMTGK (SEQ ID NO: 4) Peptide and Ribostamycin Antibiotic The peptide (R)$_9$LPMTGK (SEQ ID NO: 4) and the antibiotic, Ribostamycin, were taken in 0.05M Tris-acetate buffer (pH 7.5) (containing 150 mM NaCl, 5 mM CaCl$_2$, and 2 mM 2-mercaptoethanol) and incubated with sortase at about 37° C. for about 4-6 hours. The reaction was quenched by addition of 20 to 40-fold excess of 0.1% trifluoroacetic acid (TFA). The reaction mixture was analyzed by RPHPLC using acetonitrile-water-TFA solvent system. Reaction products obtained from RPHPLC were characterized by ESMS. The observed mass of the reaction product was 2302.9 Da and the expected theoretical mass of (R)$_9$LPMT—Ribostamycin conjugate was 2303.53 Da. The RPHPLC of the reaction mixture followed by ESMS analyses of the product indeed confirmed the formation of the expected peptide-antibiotic conjugate. (Refer table 2).

Example 15

Sortase-Catalyzed Ligation of Tat and Rev Mimetics to Antibiotics

Ligation of peptides derived from Tat and Rev protein of HIV to aminoglycoside antibiotics was considered. Tat and Rev are two essential regulatory proteins that play important roles in HIV replication. Both Tat and Rev act through structured viral RNA target sites, TAR in the case of Tat and RRE in the case of Rev (14). Short arginine rich peptide sequences derived from Tat and Rev can mimic the action of respective parent proteins (15). Besides, a nona-arginine peptide (R$_9$) is known to bind to TAR with the same affinity and specificity as the wild type Tat peptide. Since aminoglycoside antibiotics (such as neomycin, tobramycin, ribostamycin etc) also bind to TAR and RRE RNA (16), bio-conjugates consisting of aminoglycoside antibiotics and Tat and/or Rev peptide mimics (natural or designed) are likely to exert synergistic action and be potent inhibitors of HIV replication.

Figure 9:
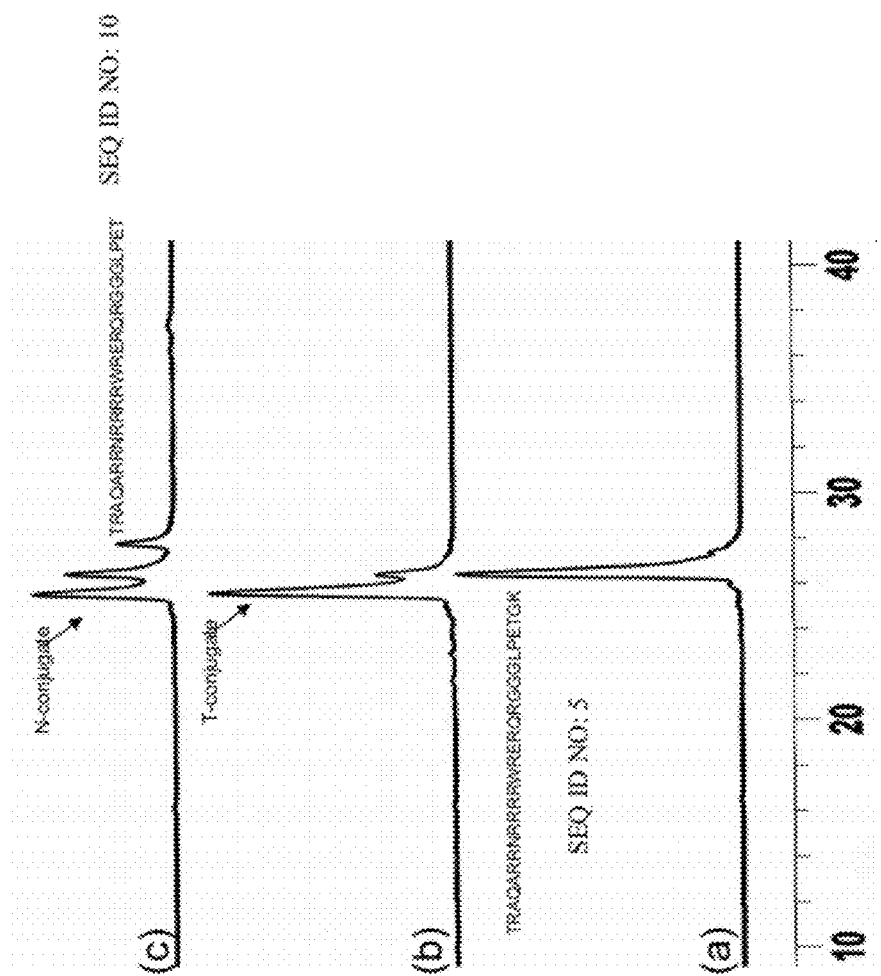
FIG. 9 shows RPHPLC analyses of sortase catalysed conjugation of Rev-LPXTG peptide to tobramycin and neomycin B.

The sortase-catalyzed ligation reaction of a non-arginine sequence carrying a sortase recognizable LPXTGK (SEQ ID NO: 17) (X=E or M) motif (RRRRRRRRRLPXTGK (SEQ ID NO: 18)) with the antibiotics proceeded in much the same way as the model peptide substrate [(FIG. 9 (b)]. Likewise, a peptide sequence spanning residues 34-50 of Rev and appended with the sortase recognition sequence (TRQAR-RNRRRRWRERQRGGGLPETGK, SEQ ID NO: 5) also formed specific conjugates with neomycin B and tobramycin [FIG. 9(c)] The experimental mass of the conjugates was in accord with the calculated mass (Table 2).

Example 16

Peptide Ligation to Amikacin and Butirosin A

Figure 7:
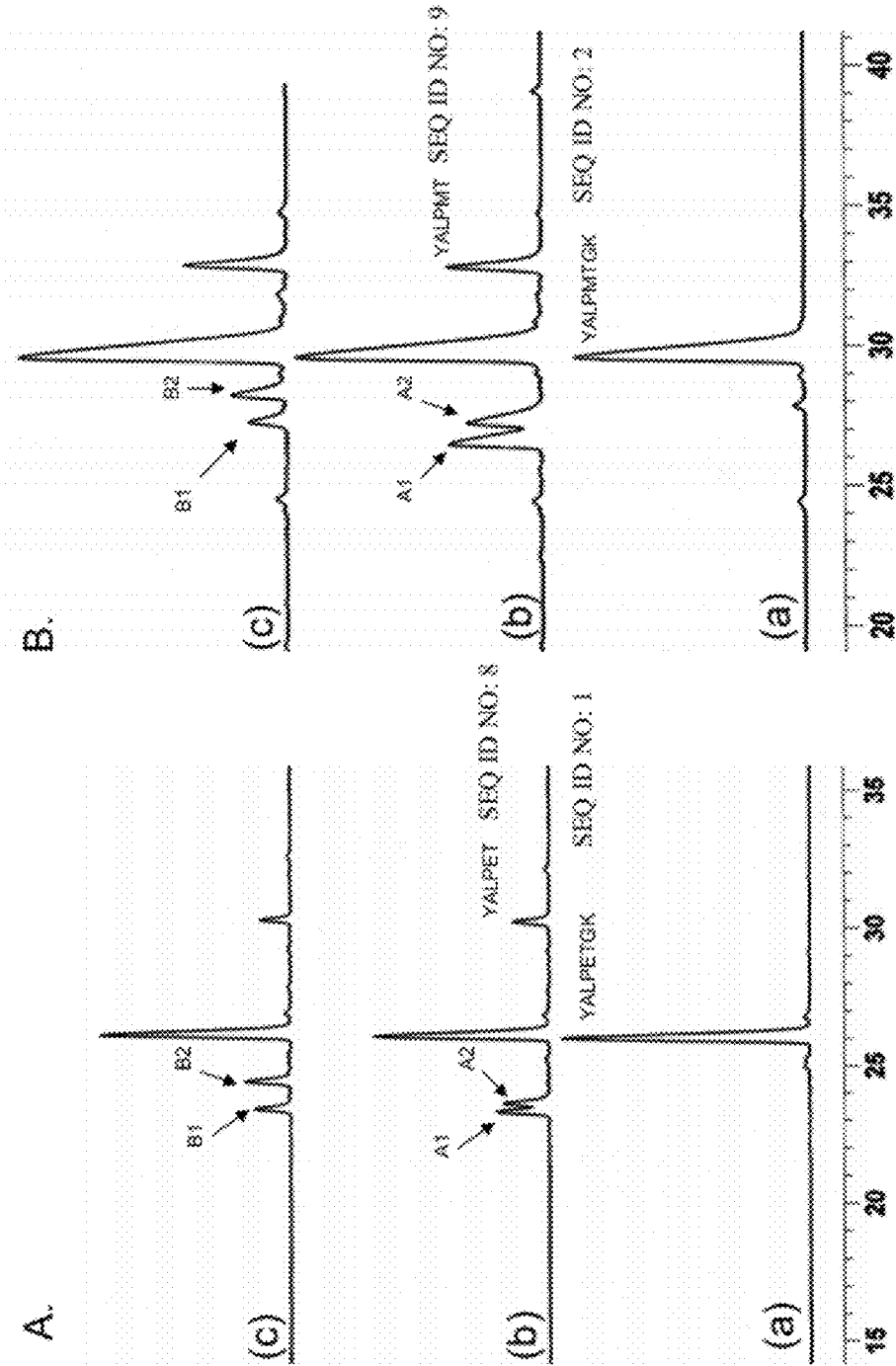
FIG. 7 shows RPHPLC analyses of Sortase-catalyzed ligation reaction of LPXTG (SEQ ID NO: 11) peptides to amikacin and butirosin A.
Figure 8:
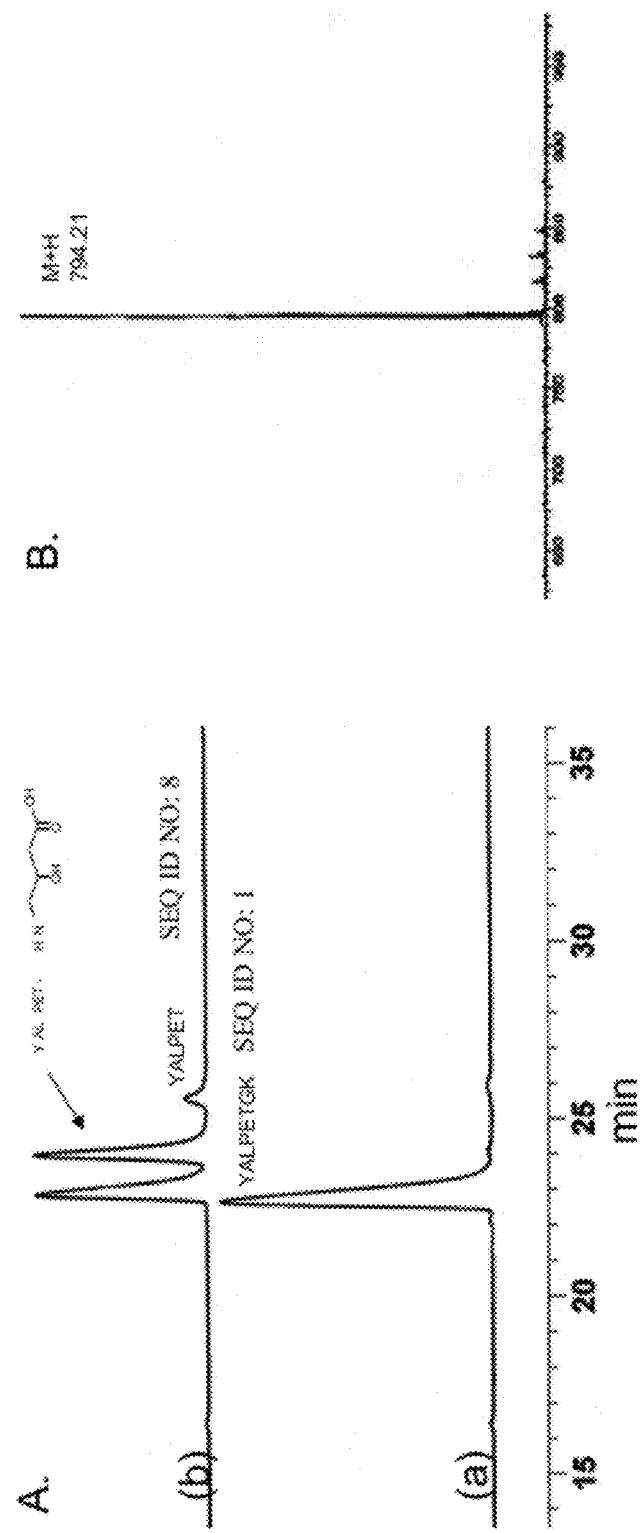
FIG. 8 shows analyses (RPHPLC and mass) of Sortase-catalyzed ligation reaction of YALPETGK (SEQ ID NO: 1) peptide to 4-amino-3-hydroxybutyric acid.

The sortase-catalyzed ligation of peptides to amikacin and butirosin A was investigated. These antibiotics, of the kanamycin and ribostamycin class respectively, are unique in that they carry a 4-amino-2-hydroxybutyrate (ahba) side chain on the C-1 amino group of the central deoxystreptamine ring. Unlike the peptide ligation reactions with antibiotics described above, the HPLC chromatographic profile of sortase peptide substrates (YALPXTGK (SEQ ID NO: 19), X=E or M) reacted with amikacin or butirosin A showed two product peaks [FIGS. 7, A and B] Interestingly, both the product peaks of each antibiotics yielded identical mass (1260.67 Da in the case of amikacin and 1230.67 Da in the case of butirosin A) corresponding to a 1:1 ligation of the peptide to antibiotics when analyzed by MALDI. The results suggest that each product represented a distinct site of peptide ligation. Given that the difference between their respective parent antibiotics (kanamycin and ribostamycin) was the presence of ahba group, the two products may represent conjugation of peptide either to the 6-amine in the A-ring or the amine of the ahba side chain of the 6-deoxystreptamine ring. Consistent with this, sortase was able to transfer relevant peptide substrate to 4-amino-2-hydroxybutyric acid as well as to 4-amino-3-hydroxybutyric acid (FIG. 8).

Example 17

Sortase-Catalyzed Peptide Ligation to Polyamine Spermine

Figure 10:
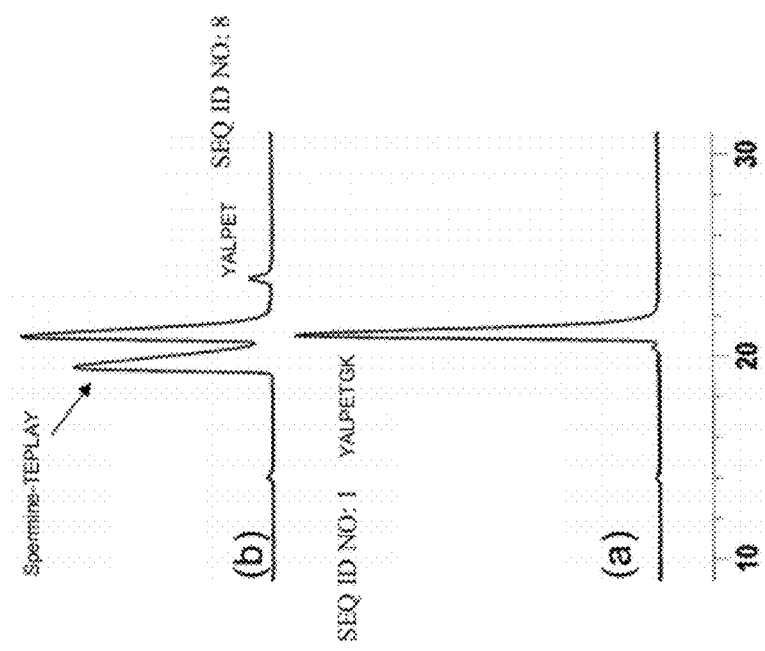
FIG. 10 shows analyses (RPHPLC and mass) of Sortase-catalyzed ligation of YALPETGK (SEQ ID NO: 1) with spermine.

We also explored the ability of sortase to conjugate peptide substrate to polyamines. The HPLC profile of a reaction mixture incubated with YALPETGK (SEQ ID NO: 1) peptide and spermine revealed the formation a product which was characterized by ESMS as a spermine-peptide adduct (FIG. 10, Table 2).

TABLE 1

ESI mass analyses of synthetic peptides used in sortase-mediated ligation reactions

| SEQ ID NO | Sequence | Observed | Calculated |
|---|---|---|---|
| 1 | YALPETGK | 877.55 | 877.99 |
| 2 | YALPMTGK | 879.53 | 880.07 |
| 3 | RRRRRRRRRLPETGK | 2049.01 | 2049.42 |
| 4 | RRRRRRRRRLPMTGK | 2051.28 | 2051.50 |
| 5 | TRQARRNRRRRWRERQRGGGLPETGK | 3234.24 | 3234.64 |

TABLE 2

ESI mass of sortase-catalyzed ligation product formed from LPXTG (SEQ ID NO: 11) containing peptides and various amino nucleophiles

| Peptide | Nucleophile | Product | Observed mass (Da) | Expected mass (Da) |
|---|---|---|---|---|
| YALPMTGK (SEQ ID NO: 21) | adg | adg-TMPLAY | 855.62 | 855.85 |
| YALPMTGK (SEQ ID NO: 21) | Kanamycin A | Kanamycin A-TMPLAY | 1160.34 | 1161.64 |
| YALPMTGK (SEQ ID NO: 21) | Kanamycin B | Kanamycin B- TMPLAY | 1159.93 | 1160.64 |
| YALPMTGK (SEQ ID NO: 21) | Tobramycin | Tobramycin- TMPLAY | 1144.03 | 1144.35 |
| YALPMTGK (SEQ ID NO: 21) | Paromomycin | Paromomycin- TMPLAY | 1292.09 | 1292.47 |
| YALPMTGK (SEQ ID NO: 21) | Ribostamycin | Ribostamycin- TMPLAY | 1130.86 | 1131.31 |
| YALPMTGK (SEQ ID NO: 21) | Neomycin B | Neomycin B- TMPLAY | 1290.74 | 1291.48 |
| $R_9$LPMTGK (SEQ ID NO: 22) | Tobramycin | Tobramycin- TMPL$R_9$ | 2315.90 | 2315.79 |
| $R_9$LPMTGK (SEQ ID NO: 22) | Paromomycin | Paromomycin- TMPL$R_9$ | 2463.17 | 2463.91 |
| $R_9$LPMTGK (SEQ ID NO: 22) | Ribostamycin | Ribostamycin- TMPL$R_9$ | 2302.92 | 2303.75 |
| $R_9$LPETGK (SEQ ID NO: 23) | Neomycin B | Neomycin B- TEPL$R_9$ | 2460.03 | 2460.84 |
| YALPETGK (SEQ ID NO: 24) | adg | adg- TEPLAY | 853.37 | 853.76 |
| YALPETGK (SEQ ID NO: 24) | Kanamycin A | Kanamycin A- TEPLAY | 1158.49 | 1159.26 |
| YALPETGK (SEQ ID NO: 24) | Tobramycin | Tobramycin- TEPLAY | 1142.27 | 1141.57 |
| YALPETGK (SEQ ID NO: 24) | Ribostamycin | Ribostamycin- TEPLAY | 1128.56 | 1129.23 |
| YALPETGK (SEQ ID NO: 24) | Paromomycin | Paromomycin- TEPLAY | 1289.63 | 1290.39 |
| YALPETGK (SEQ ID NO: 24) | Neomycin B | Neomycin B- TEPLAY | 1288.63 | 1289.4 |
| Rev-LPETGK (SEQ ID NO: 25) | Tobramycin | Tobramycin- TEPL-Rev | 3498.30 | 3498.93 |
| Rev-LPETGK (SEQ ID NO: 25) | Neomycin B | Neomycin B- TEPL-Rev | 3646.55 | 3646.06 |
| YALPETGK (SEQ ID NO: 24) | ahba | ahba- TEPLAY | 793.21 | 793.88 |
| YALPETGK (SEQ ID NO: 24) | Spermine | Spermine- TEPLAY | 876.89 | 877.10 |
| YALPETGK (SEQ ID NO: 24) | adm | adm-TEPLAY | 853.94 | 853.57 |

Abbreviations used in the table: adg, 6-amino-6-deoxyglucose; adm, 6-amino-6-deoxymannose; Rev, TRQARRNRRRRWRERQRGGG (SEQ ID NO: 20); ahba, 4-amino-3-hydroxybutyric acid; Spermine, N,N'-Bis(3-aminopropyl)-1,4-butanediamine.

What is claimed is:

1. A novel therapeutic and diagnostic bioconjugate useful for target delivery of a compound, wherein said bioconjugate comprising:
   a. a substrate comprising LPXTG (SEQ ID NO: 11) peptide motif capable of recognizing sortase, wherein said substrate is selected from a group consisting of peptides, polypeptides, proteins, glycoprotein, lipoprotein, antibodies, radionucleotides, fluorophores, ligand chromophore and any compound comprising the LPXTG (SEQ ID NO: 11) peptide motif; and
   b. a biomolecule that is an aminoglycoside having a 6-Deoxy-6-amino-hexose moiety, wherein the glycine moiety of the LPXTG (SEQ ID NO: 11) motif is cleaved and the substrate is attached to the biomolecule via an amide bond between the resulting terminal threonyl carboxylate and the biomolecule to form the bioconjugate.

2. The bioconjugate as claimed in claim 1, wherein the substrate is a peptide having amino acid sequence selected from a group consisting of SEQ ID NO: 1, SEQ ID NO:2, SEQ ID NO: 3, SEQ ID NO: 4 and SEQ ID NO: 5.

3. The bioconjugate as claimed in claim 1, wherein the aminoglycoside is selected from a group consisting of ribostamycin, butirosin, paromomycin, neomycin, lividomycin, kanamycin, tobramycin, dibekacin, sismocin, arbekacin, amikacin, streptomycin, apramycin, hygromycin, neamine, vancomycin and kasugamycin.

4. The bioconjugate as claimed in claim 1, wherein the aminosugar is selected from a group consisting of 6-amino-6-deoxyglucose, 6-amino-6-deoxymannose, 6-amino-6-deoxyallose, 6-amino-6-deoxyaltrose, 6-amino-6-deoxyidose, 6-amino-6-deoxygalactose and 6-amino-6-deoxytalose.

5. The bioconjugate as claimed in claim 1, wherein the hydroxyamino acid is selected from a group consisting of 4-amino-3-hydroxybutyric acid, 4-amino-2-hydroxybutyric acid and etahnolamine.

6. The bioconjugate as claimed in claim 1, wherein the hydroxyamino acid ester is selected from a group consisting of 4-amino-3-hydroxybutyryl stearate, 4-amino-3-hydroxybutyryl palmitate, 4-amino-3-hydroxybutyryl acetate, 4-amino-3-hydroxybutyryl propionate, butyrate/ or 4-amino-2-hydroxybutyryl-acetate, 4-amino-2-hydroxybutyryl-propionate, 4-amino-2-hydroxybutyryl-butyrate, 4-amino-2-hydroxybutyryl-stearate, 4-amino-2-hydroxybutyrylpalmitate, 4-amino-2-hydroxy-butyryl-coenzyme A, 4-amino-3-hydroxybutyrylpalmitate, 4-amino-2-hydroxybutyryl-coenzyme A.

7. The bioconjugate as claimed in claim 1, wherein the aminolipid is either N-[(3-hexadecanoyloxy)hexadecanoyl] ornithine or virodhamine.

8. A process of preparing the bioconjugate as claimed in claim 1, said process comprising:
   a. providing a substrate comprising LPXTG peptide motif capable of recognizing sortase, wherein said substrate is selected from a group consisting of peptides, polypeptides, proteins, glycoprotein, lipoprotein, antibodies, radionucleotides, fluorophores, ligand chromophore and any compound comprising the LPXTG peptide motif;
   b. providing a biomolecule selected from a group consisting of aminoglycosid aminosugar, hydroxyamino acid, hydroxyamino acid ester and aminolipid;
   c. providing sortase to catalyze the ligation reaction of said substrate and said biomolecule under suitable conditions to obtain said bioconjugate.

9. The process of preparing the bioconjugate as claimed in claim 8, wherein the sortase is isolated from *Staphylococcus aureus*.

10. The process of preparing the bioconjugate as claimed in claim 9, wherein the substrate is a peptide comprising an amino acid sequence as set forth in SEQ ID NO: 1 or SEQ ID NO: 2 or SEQ ID NO: 3 or SEQ ID NO: 4 or SEQ ID NO: 5.

11. The process of preparing the bioconjugate as claimed in claim 10, wherein the aminoglycoside is selected from a group consisting of ribostamycin, butirosin, paromomycin, neomycin, lividomycin, kanamycin, tobramycin, dibekacin, gentamicin, sismocin, netilimicin, isepamicin, arbekacin and amikacin.

12. The process of preparing the bioconjugate as claimed in claim 10, wherein the aminosugar is selected from a group consisting of 6-amino-6-deoxyglucose, 6-amino-6-deoxymannose, 6-amino-6 deoxyallose, 6-amino-6-deoxyaltrose, 6-amino-6-deoxyidose, 6-amino-6-deoxygalactose and 6-amino-6-deoxytalose.

13. The process of preparing the bioconjugate as claimed in claim 10, wherein the hydroxyamino acid is selected from a group consisting of 4-amino-3-hydroxybutyric acid, 4-amino-2-hydroxybutyric acid and etahnolamine.

14. A composition useful as therapeutic or diagnostic agent comprising the bioconjugate as claimed in claim 1 and pharmaceutically acceptable carrier.

15. A kit useful for therapy or diagnosis comprising said bioconjugate as claimed in claim 1 and reagents suitable for administering said bioconjugate to an individual.

* * * * *